United States Patent [19]
Cardellini et al.

[11] Patent Number: 5,363,696
[45] Date of Patent: Nov. 15, 1994

[54] METHOD AND ARRANGEMENT FOR OIL WELL TEST SYSTEM

[75] Inventors: David A. Cardellini, Hunnington Beach; Michael P. Biencourt, Chino; Jeffrey P. Taylor, Trabuco Canyon, all of Calif.; John A. Haeber, Roseburg, Oreg.; John A. DeVires, Tustin, Calif.

[73] Assignee: Paul-Munroe Engineering, Orange, Calif.

[21] Appl. No.: 124,958

[22] Filed: Sep. 21, 1993

[51] Int. Cl.$^5$ ............................................. G01N 27/22
[52] U.S. Cl. ..................................... 73/61.44; 364/510
[58] Field of Search ........................ 73/61.44; 364/510

[56] References Cited

U.S. PATENT DOCUMENTS

| | | | |
|---|---|---|---|
| 3,911,256 | 10/1975 | Jones | 73/61.44 X |
| 4,215,567 | 8/1980 | Vlcek | 73/61.44 |
| 4,836,017 | 6/1989 | Bozek | 73/61.44 X |
| 4,852,395 | 8/1989 | Kolpak | 73/61.44 |
| 5,090,238 | 2/1992 | Jones | 73/61.44 X |
| 5,211,842 | 5/1993 | Tuss et al. | 73/61.44 X |
| 5,263,363 | 11/1993 | Agar | 73/61.44 |

FOREIGN PATENT DOCUMENTS 9002941 3/1990 WIPO ................................. 73/61.44

Primary Examiner—Thomas P. Noland
Assistant Examiner—Joseph W. Roskos
Attorney, Agent, or Firm—Gilliam, Duncan & Harms

[57] ABSTRACT

An improved method and arrangement for calculating the fluid phase fractions of gas, oil, and water and oil-water emulsion in a fluid steam flowing from an oil well which includes separating out the majority of gas from the well stream and repeatedly trapping a sample of the primarily resultant liquid well stream in a vertically disposed sampling chamber. The well stream sample is held therein to permit separation of the phase fractions to the extent possible within a reasonable time. A number of measurements of the well stream sample are taken. In addition, a number of measurements are taken of the capacitance at a plurality of discrete vertically spaced locations within the sampling chamber. These capacitance measurements relate directly to the varying permitivity of the phase fractions of gas, oil, and water and the oil-water emulsion of the sample. The measurements are processed by a data processor to provide precise information on such phase fractions and emulsion interfaces.

20 Claims, 4 Drawing Sheets

METHOD AND ARRANGEMENT FOR OIL WELL TEST SYSTEM

BACKGROUND

The present invention relates to an improvement in the field of testing oil well streams and more particularly, but not by way of limitation, to a novel method and automated system for determining the phase fractions of gas, oil, and water and oil-emulsion of an oil well stream.

It is well known that in the majority of oil wells, the fluid flowing or being pumped from an oil well is not pure oil but is a mixture of gas, oil water, gas, chemicals and at times solids. While the gas, oil, and water do occur in a free state quite often these items often flow in an emulsion condition. It is also well known that it is important to monitor the production or flow of a particular oil well or a plurality of oil wells in a particular field or region. The net oil production from a well must be determined as well as the volume of oil, gas, and water that are present in the well stream.

The oldest and most widely accepted method of testing oil well production fluids was the three phase separator tank arrangement which consisted primarily of a large receiving tank into which a predetermined well stream flowing from an oil well would be deposited and allowed to stand. The effect of gravity on the sample would cause the free water to settle to the bottom of the tank, the oil to rise to the top of the settled water, and the gas to rise above the oil. This arrangement was commonly referred to as a three phase separator. The gas is allowed to escape from the tank and the remaining volummes of water and crude oil are measured. The crude oil was tested to determine its water content or wetness by a capacitance probe. Other factors of the test sample were also measured and a fair estimate of the net oil being produced was made.

The three phase separator was prone to a number of shortcomings. Such an apparatus was large and cumbersome and required the exercise of care by skilled technicians in its operation. The time required for the emulsions, oil, water, and gas of a well stream to separate adequately often required many hours or days. Also, the capacitance probes employed were extremely sensitive to certain external factors and were not dependable. The end result was that the method yielded the net oil of a production on about 75% of wells tested with a margin of error of about 10%.

More recently, U.S. Pat. No. 3,911,256 presented an improved apparatus for testing and analyzing a well stream. This patent provided for diverting a predetermined volummetric portion of the flow of a well stream and then measuring the pressure of the isolated portion. This portion was then subjected to compression of the gas fraction so that the volume of gas could be mathematically determined. Other measurements were made of the test portion so that the volume of gas and proportions of each liquid in the well stream test portion could be determined by mathematical comparative calculations.

U.S. Pat. No. 4,852,395 discloses a three phase fluid flow measuring system for measuring the volummetric fractions of gas, water and oil which included a centrifugal separator for conducting primary separation of gas from the liquid phase. A sample of the resultant fluid stream was conducted to a test chamber where it was subjected to an increased pressure. The transmissivity of microwave energy through the test sample was then measured as a way of determining the gas phase in the liquid phase and to determine the volummetric fraction of water and oil in the liquid phase.

It is also known in the art to segregate a test sample of a well stream and to record the flow rate, temperature, pressure, and weight of such sample and to also determine the aggregate capacitance of the sample. The net oil, gas, and water content are then determined mathematically, after corrections for temperature.

However, all known prior art systems and methods are subject to a number of shortcomings. Some systems will not provide accurate liquid flow data if the well stream produces over a 5% gas fraction or if the fluids do not separate into oil and water fractions by the force of gravity within a five minute period. Also, inaccurate data is obtained as the degree of emulsion of the fluids increases or varies.

In addition, the prior art systems are temperature dependant. As the test chamber or test probes are fouled by oil build up, test readings begin to vary unacceptably. Great difficulties have been experienced in calibrating capacitance probes which require a cumbersome difficult procedure. Also, recalibration of current systems must be made in the event that the capacitance of the oil or water changes over time, or with the addition of chemicals into the well stream. However, the biggest problem remains with emulsions that remain after the time permitted for separation of the fractions and the inconsistencies in capacitance readings that result in indicating a larger water content than is actually present.

While the prior patents and prior art commercial devices have been successful to a certain extent, it is nonetheless clear that substantial room exists for affecting an advance in the art which overcomes these shortcomings in a practical and efficient manner.

It is a general object of the invention to provide an improved method and system for testing and analyzing oil production fluid to determine the net oil content thereof and which overcomes many of the shortcomings that are found in the methods and apparatus of the known prior art.

Another object of the invention is to provide an improved method and automated system for determining the phase fractions of an oil well stream wherein the gas, water, and oil fractions of a test sample of the well stream are not separated nor need to be separated in the process of analyzing and calculating the new oil content.

Yet another object of the invention is to provide a method and system which may accurately test and analyze test well samples which have gas fractions from 0 to 100% of the total well production volume.

Another object of the invention is to provide and improved method and system for analyzing a production well stream which will reduce or substantially minimize the effects of any accumulated oil coating on the interior of the test chamber.

It is a further object of the invention to provide a method of analyzing a test sample of a production well stream which will provide additional data beyond the phase fractions of gas, oil and water and which will minimize the dependency on entry of accurate data relating to the densities of oil, gas and water, permitivity of oil, water, gas, etc. thereby providing "live" oil and water density data.

Also, it is an object of the improved method to permit analysis and quantification of the degree of oil-water emulsion of the test sample of the well stream and to indicate the separation rate of the oil and gas fractions.

The foregoing has outlined some of the more pertinent objects of the invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with the specific embodiments shown in the attached drawings. Briefly stated, the present invention contemplates a novel method and system for calculating the fluid phase fractions of gas, oil, and water and oil-water emulsion in an oil well production fluid stream flowing from an oil well which includes separating out the majority of gas from the well stream with the separated gas being measured as it flows into an outlet conduit for the testing system. The remaining fluid stream is then directed through a metering outlet for introduction into the outlet conduit of the test system and is intermittently sampled by introducing a test sample into a vertically disposed sampling chamber so that it forms a liquid column sample of the fluid stream. The fluid test sample is held in the sampling chamber for a limited time to permit settling of solids and separation of fractions and dissipation of emulsions commensurate with an acceptable testing rate.

Measurements of the fluid sample are taken to determine the absolute temperature, absolute pressure, differential pressure generated by a known liquid column height and in, addition, one physical feature is measured over the vertical height of the sample. In the illustrated embodiments of the invention, this feature is provided by measuring the capacitance of the sample at a number of discrete spaced locations over the height of the sample, with the capacitance being representative of the permitivity of the fluid sample at each location. The measurements taken are then used by a data processor to solve a plurality of linear equations and thereby reveal the phase fractions of gas, oil and water and the oil-water emulsion of the test sample. Such measurements permit the volummes of such constituents to be accurately calculated and to clearly reveal the interfaces of such constituents and the oil-water emulsion and the rate of separation.

After testing is completed on the sample the sampling chamber is exhausted to the outlet conduit of the system and the testing chamber is purged of the previous sample as the fluid stream from the gas separation chamber is reintroduced. The testing procedure is repeatedly conducted with the test results being summed and averaged to provide a representative real time understanding of the well stream and its phase fractions.

The foregoing has outlined rather broadly the more pertinent and important features of the present invention in order that the detailed description of the invention that follows may be better understood so that the present contribution to the art may be more fully appreciated. Additional features of the invention will be described hereinafter which form the subject of the claims of the invention. It should be appreciated by those skilled in the art that the conception and the disclosed specific embodiment may be readily utilized as a basis for modifying or designing other structures and methods for carrying out the same purposes of the present invention. It should also be realized by those skilled in the art that such equivalent constructions and methods do not depart from the spirit and scope of the invention as set forth in the appended claims.

BRIEF DESCRIPTION OF THE DRAWINGS

For a fuller understanding of the nature and objects of the invention, reference should be had to the following detailed description taken in conjunction with the accompanying drawings in which.

Similar numerals refer to similar parts in the various embodiments.

DETAILED DESCRIPTION OF THE INVENTION

Figure 1:
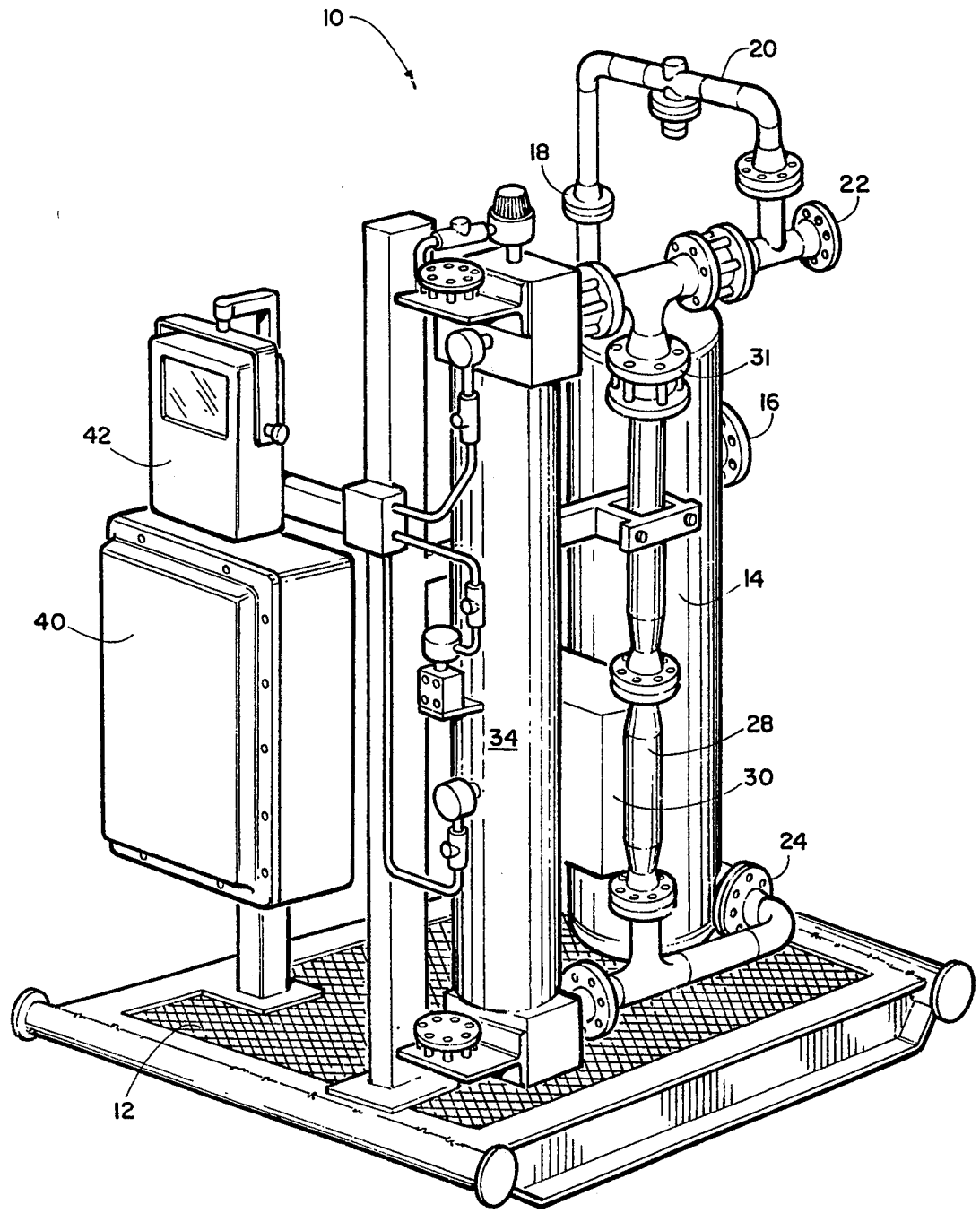
FIG. 1 is a simplified perspective of an automated test arrangement for determining the gas, oil and water phase fractions of an oil well flow stream.
Figure 2:
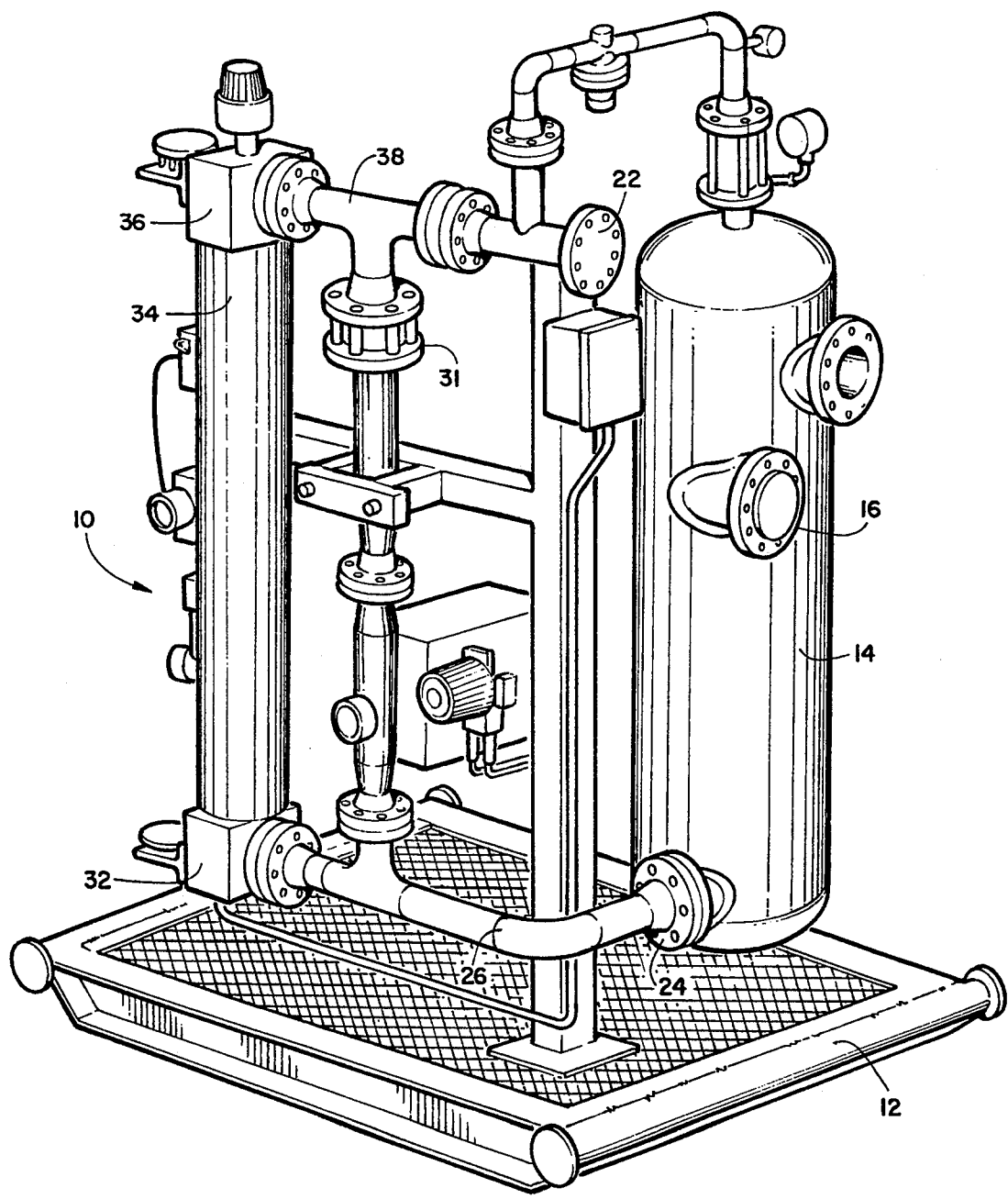
FIG. 2 is another simplified perspective of the automated test arrangement shown in FIG. 1.

Referring now to the drawings in detail, and in particular to FIGS. 1 and 2, the reference character 10 generally designates an automated sampling and testing arrangement constructed in accordance with a preferred embodiment of the invention for carrying out the novel method of the invention. The arrangement 10 which may be placed on a suitable skid 12 for ease of placement at a well site having one or a plurality of producing oil wells. The arrangement 10 includes a first phase separator 14 having an inlet 16 for receiving a fluid stream directly from a producing oil well. It is to be understood that while the arrangement 10 will be described with reference to testing a single well, a suitable arrangement (not shown) may be provided to test sequentially a plurality of oil wells of an oil field. This would be particularly desirable when a particular operation such as water flooding was being conducted so that the effect thereof could be closely monitored with a high degree of confidence in the observed data.

The first phase separator or fluid conditioner 14 receives the well stream tangentially through the inlet 16 and acts to separate out of the well stream 95-99% of the undissolved free gas of the flow stream. The separated free gas passes upwardly out of the top of the fluid conditioner 14 to a suitable gas flow meter 18 for metering of such flow and then flows through conduit 20 into a fluid conduit 22 for the entire test arrangement 10.

The primarily liquid stream remaining after such gas separation is then routed from the fluid conditioner through outlet 24 at the lower portion of the conditioner 14. The outlet 24 is connected to conduit 26 which in turn is coupled to a metering leg 28 provided with a suitable gross flow meter 30 which continuously meters the flow of the degassed liquid well stream. The metering leg 28 is connected to the fluid outlet 22 of the testing arrangement for outflow of the metered liquid stream which then flows with the metered gas stream out of the arrangement 10. The flow of liquid well stream through the metering leg 28 is controlled by a suitable valve 31 interposed therein.

The conduit 26 is also connected through a suitable inlet valve 32 to a vertically disposed sampling chamber 34 which selectively traps a sample of the separated liquid well stream for analysis. The sampling chamber 34 is provided with a selectively actuated outlet valve 36 to permit flow from the sampling chamber 34 through pipe 38 to the fluid outlet 22 of the test arrangement.

The testing and analysis of the liquid well stream flowing from the phase separator 14 is commenced by closing the valve 31 to preclude flow of the separated liquid well stream through the metering leg 28. Simultaneously with such closing, the upper and lower valves 36 and 32 associated with the sampling chamber 34 are opened to permit the liquid well stream to flow therethrough to purge the sampling chamber 34 of whatever previous sample of the well stream that had been previously trapped therein for analysis. This step depending on the pressure of the liquid stream can be conducted relatively quickly. The valves 32 and 36 are then closed to trap a sample of the liquid well stream within the sampling chamber as the valve 31 is opened to permit flow of the liquid stream through the metering leg 28 of the arrangement 10. The sampling chamber 34 has known dimensions with the sample of the separated well steam being trapped therein in a vertical liquid column.

The trapped sample is then permitted to rest in the sampling chamber for a predetermined period of time to separate into gas, oil and water fractions. Depending upon the particular well stream, an emulsion of the oil and water is present to some extent. The time allowed for such separation will of course depend upon the number of wells being monitored, the particular well stream being analyzed, and other factors depending upon the particular application. Upon expiration of the time allotted by the arrangement 10 for separation of the phase fractions of the trapped well stream sample, a plurality of measurements are taken of certain aspects of such sample. These measurements, which are taken in a suitable conventional manner, include the absolute temperature, the absolute pressure, and the differential pressure generated by a known liquid column height. In addition, one other measurement is taken of a physical feature of the trapped sample at a plurality of spaced discrete locations 68 along the vertical height of such sample.

In the preferred embodiment of the invention, this physical feature is the electrical capacitance which is measured at each discrete location. The electrical capacitance is indicative of the permitivity of the fluid at such discrete location. These measurements are input to a suitable electrical interface 40 which is coupled to a suitable computer 42 which uses the data obtained to solve for the three unknowns in three equations as will be discussed in greater detail hereinafter. The well data may be displayed in chart form on a full size LCD computer screen (not shown) or displayed graphically by the computer 42 or further operated in any desired manner.

After the measurements have been made as above mentioned, the valves 32 and 36 are reopened and the valve 31 in the metering leg 30 is closed to purge the trapped sample from the sampling chamber 34 is purged and the cycle is repeated to refill and to test another sample. In a typical application, these tests may be conducted approximately every five minutes with about ten to twelve tests being taken every hour. The results from these real time tests are then summed and averaged by the computer 42 to provide an average for such tests.

For wells that produce at a steady rate, only a short total test period is needed, which typically may be on the order of one to two hours. For wells that produce at variable flow rates or wells which flow heads (what does flow heads mean?), longer test periods may be required. Obviously, the more variable the rate of flow, the longer the test period should be in order to provide statistically accurate results. In some cases a total test period of two to three days or even longer may be required.

Figure 3:
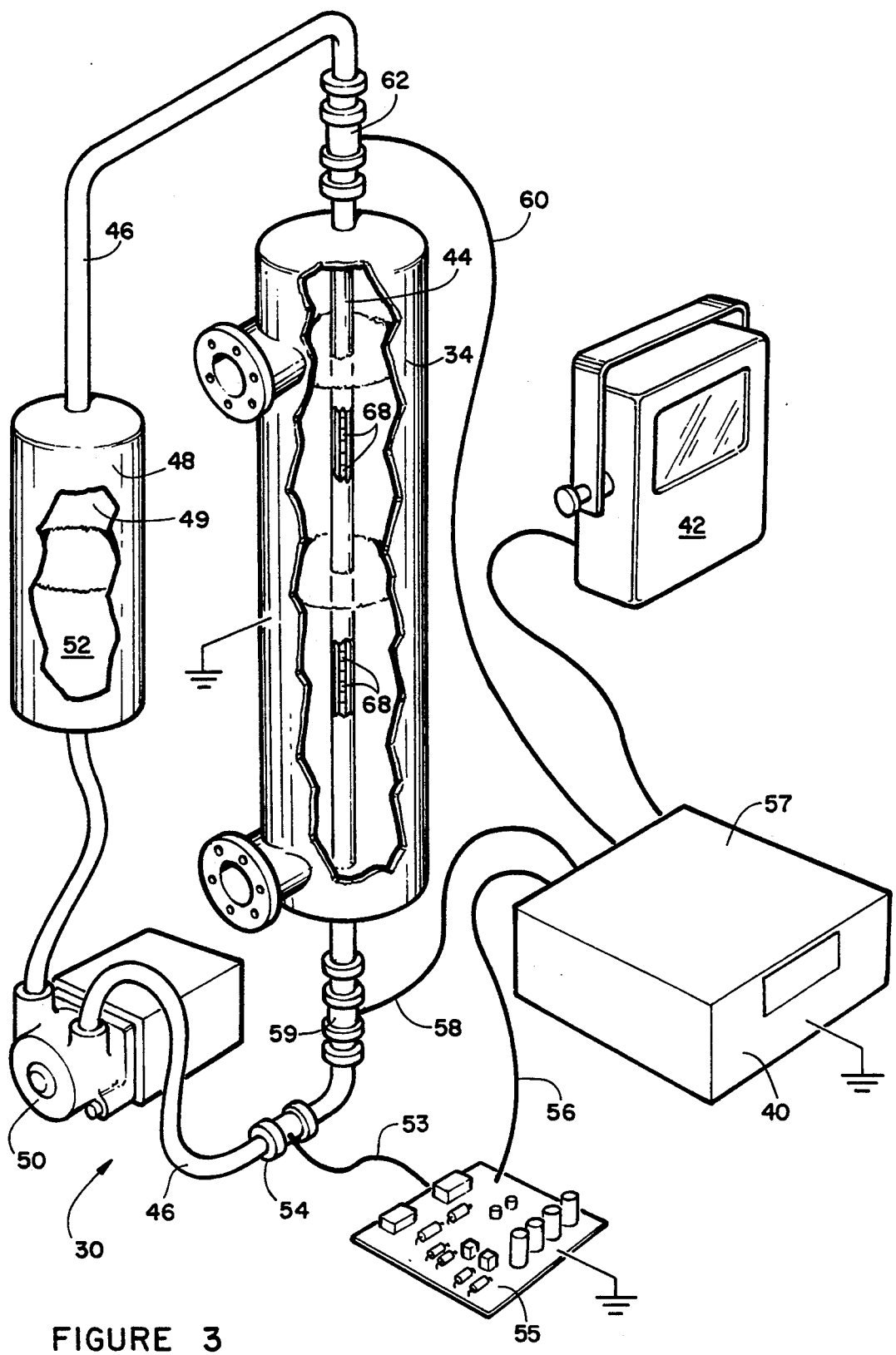
FIG. 3 is a simplified perspective of the fluid sampling and testing feature of the arrangement shown in FIGS. 1 and 2.
Figure 4:
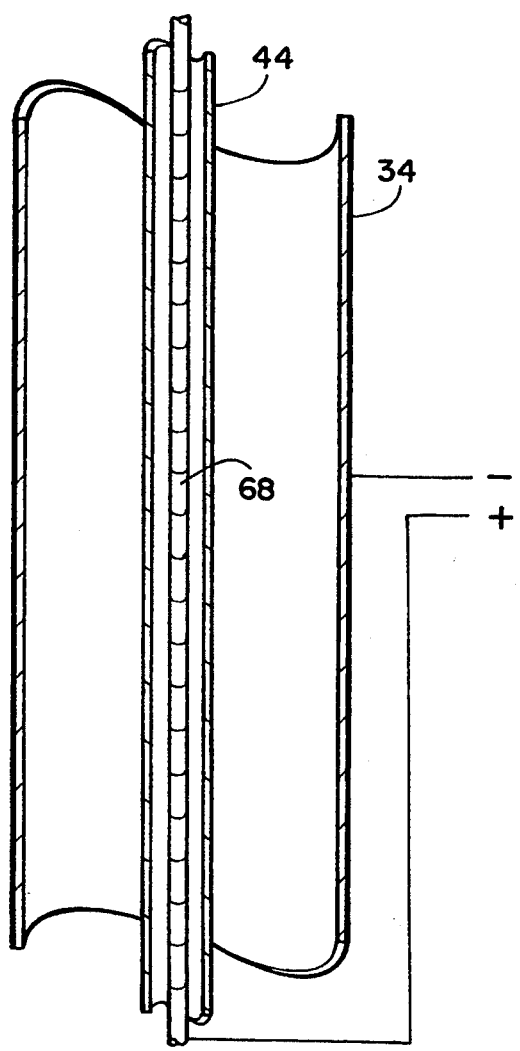
FIG. 4 is a simplified sectional view of another embodiment of the fluid sampling and testing feature.

Referring now to FIGS. 3 and 4, the novel feature of measuring the capacitance over the vertical height of the trapped well stream sample at a number of discrete locations will be discussed in greater detail. As will be seen, the sampling chamber 34 is provide with a vertically extending hollow tube 44 which extends along the vertical axis of the chamber 34. The tube 44 is electrically nonconductive and is connected at each end to tubing 46 is which is interposed a fluid reservoir 48 and a suitable reversible pump 50. A suitable conductive fluid 52, such as brine, and an organic fluid 49, such as kerosene, are contained in the reservoir 48.

A plurality of electrical capacitance indicators 68, see FIG. 4, are spaced at a plurality of discrete locations along the vertical height of the tube 44 for providing capacitance readings at each such location. Each of the capacitance indicators 68 is coupled from coupler 54 through cable 53 to capacitance measuring circuitry 55 which is connected by cable 56 to a suitable programmable logic controller 57 that is coupled to the computer 42. The capacitance measuring circuitry 55 and the controller 57 may be considered to be generally part of the electrical interface 40 to computer 42. The sample chamber 34 is grounded and the controller 60 is grounded to conductive couplings 62 and 59 provided on the tube 44 which is preferably protected by a suitable sheathing made from Teflon by cables 58 and 60 respectively.

The electrical capacitance along the length of tube 44 may then be measured when the time allowed for separations of the phase fractions of the well sample has been completed. The capacitance measurements may be conducted simultaneously in parallel or may be conducted serially in either direction. The point is that the capacitance readings provide a capacitance profile that is very good indication of the phase fractions and indicates precisely the interface between such fractions. Also, and very importantly, the capacitance profile provides a clear indication of the emulsion of the oil-water interface and the rate of separations. Thus, the novel invention can determine real time online densities of oil and water and can evaluate the degree and time relationship of oil-water emulsions since such measurements may be taken during the separation period of the sample.

Also, it would be within the scope of the invention to make the capacitance measurements as the conductive fluid 52 is being introduced into the tube 44 at a predetermined constant rate. As before, the capacitance measurements could be taken simultaneously in parallel or serially as the conductive fluid rises within the tube 44. As soon as the capacitance measurements have been made of the full vertical height of the sampling chamber to provide an indication of the gas, oil and water fractions and the oil-water emulsion of the sampler the pump 50 is reversed to return the brine 52 to the reservoir 48. The pump 50 could also be interposed in the tubing 46 on the other side of reservoir 48 so that the pump 50 would not be exposed to the conductive fluid 52.

The capacitance readings are indicative of the permitivity of the gas, oil and water. As is known, the fractions of gas, oil and water are related to each other by three simultaneous, linear equations. The three equations are:

$$For + Fw + Fg = 1 \tag{1}$$

$$For*Rho_o + Fw*Rho_w + Fg*Rho_g = Rho_s \tag{2}$$

$$For*Eo + Fw*Ew + FgEg = Es \tag{3}$$

Where:
For = Fraction of oil to be found
Fw = Fraction of water to be found
Fg = Fraction of gas to be found
$Rho_o$ = Known density of oil
$Rho_w$ = Known density of water
$Rho_g$ = Known density of gas
Eo = Known permitivity of oil
Ew = Known permitivity of water
Eg = Known permitivity of gas
$Rho_s$ = Measured aggregate density in the sampling chamber
Es = Measured capacitance in the sampling chamber Referring now to FIG. 4, another embodiment the method of measuring the capacitance at a plurality of spaced locations along the vertical height of the liquid sample will be described. In FIG. 4, the sampling chamber 34 is grounded to provide an anode and the central tube 44 is conductive with a nonconductive coating such as Teflon. A plurality of spaced capacitance probes are spaced along the interior of the tube 44 at n locations. The capacitance probes 52 it will be understood are suitably coupled to the programmable logic controller 60 and to the computer 42. The measurements of capacitance at discrete locations along the interior of the tube 44 may be made serially or simultaneously when the sample is trapped in the chamber 34 during or after a period of separation or during the filling of the chamber 34. The computations of the phase fractions and the oil-water emulsion are conducted as before.

Figure 5:
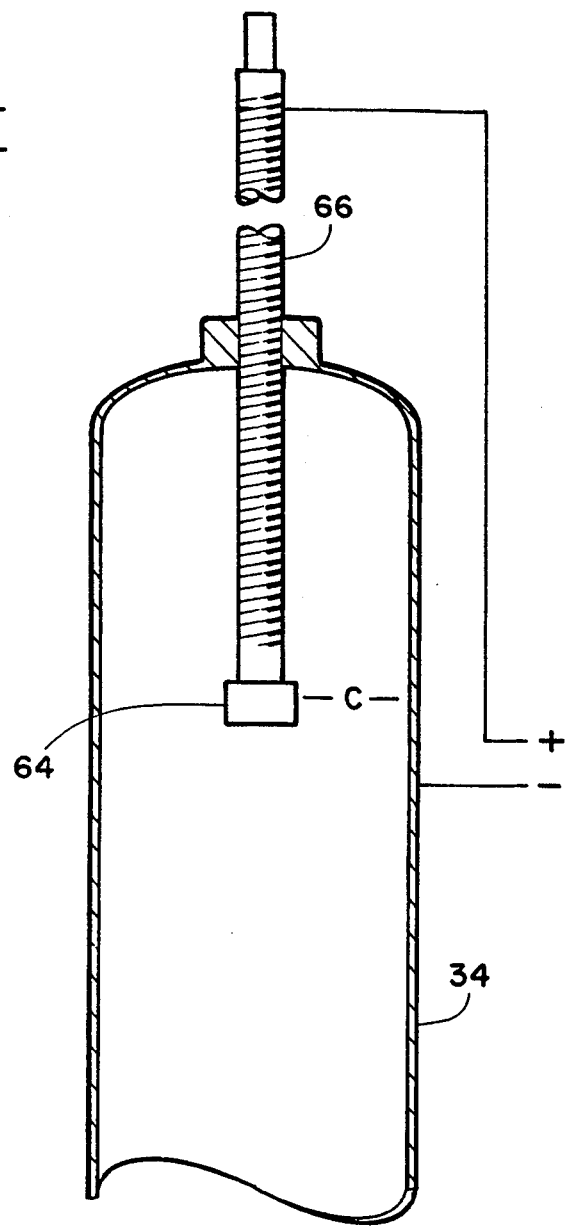
FIG. 5 is a simplified sectional view of another embodiment of the fluid sampling and testing feature.

Referring now to FIG. 5, another embodiment is shown for taking capacitance readings along the vertical longitudinal axis of the sample contained in the sampling chamber 34. Here, the sampling chamber is grounded and a conductive rod 62 having a capacitance probe 64 that is electrically coupled to the programmable logic controller 60 and to the computer 42 is positioned on the lower end of the rod 62. After the sample to be tested is trapped in the sampling chamber 34, the rod 62 is lowered into the sample at a predetermined constant velocity and measurements are made at a plurality of spaced locations along the vertical axis of the vertical liquid well stream column. The computations are conducted as before to determine the phase fractions of gas, oil and water and the oil-water emulsion.

The foregoing has illustrated a number of methods of measuring the capacitance of a liquid sample at a number spaced locations along the vertical axis of a vertical column of a well stream sample and the novel method and arrangement for determining the phase fractions of gas, oil and water and oil-water emulsion of a well stream. The novel method and arrangement makes it possible to determine accurately such flow fractions when the gas fraction is 0–100% or the oil fraction is 0–100% or the water fraction is 0–100%. The capacitance profile thus provided makes it possible to determine such phase fractions and the oil-emulsion interface on a real time basis and also makes the general mathematical equations for solving for such phase fractions less dependent on other physical measurements that may not be entirely reliable due to changing conditions.

The present disclosure includes that contained in the appended claims as well as that of the foregoing description. Although this invention has been described in its preferred forms with a certain degree of particularity, it is understood that the present disclosure of the preferred form has been made only by way of example and numerous changes in the details of construction and combination and arrangement of parts and method steps may be resorted to without departing from the spirit and scope of the invention.

What is claimed is:

1. A method for calculating the fluid phase fractions of gas, oil, and water and oil-water emulsion in an oil well production fluid stream flowing from an oil well which comprises:
    separating out the majority of gas from the well stream;
    introducing the remainder of the well stream into a vertically disposed sampling chamber having a predetermined volume and height for a predetermined period of time to purge the chamber of any fluid it may have previously contained;
    closing the chamber to trap a sample of the well stream therein as a fluid column;
    holding the well stream sample in the chamber for a predetermined period of time to permit the same to separate in such period into vertically disposed layers of gas, oil and water;
    measuring at least one physical feature of the sample at a plurality of points along the vertical length of the sample;
    determining a plurality of other measurements of the well stream sample relating to such fluid column sample, and employing such measurements to calculate the fluid phase fractions of gas, oil, and water and the oil-water emulsion in the well stream sample.

2. The method of claim 1 wherein the plurality of other measurements taken of the fluid column sample include the differential pressure generated by the height of the vertical sample column for purposes of calculating the density of the sample.

3. The method of claim 2 wherein the plurality of other measurements taken of the fluid column sample further includes measuring the absolute temperature.

4. The method of claim 3 further includes measuring the absolute pressure of the fluid column sample within the chamber.

5. The method of claim 4 which further provides repeating the plurality of other measurements taken of the fluid column sample a predetermined number of times over a predetermined period of time to obtain a plurality of values for the gas, oil and water phase fractions for a single well stream, and summing and averaging such values to obtain representative values of such well stream.

6. The method of claim 1 which further includes directing the well stream, after the gas separation step and fluid sampling step have been completed, into an outlet;

metering the gas flow initially separated from the well stream, and introducing the gas flow, after the metering step has been completed, into the outlet.

7. The method of claim 1 wherein the measurement of at least one physical feature of the sample includes determining the capacitance of the sample at a plurality of spaced discrete locations along the vertical axis of the sample.

8. The method of claim 7 wherein determination of the capacitance at discrete locations along the vertical axis of the sample is made serially.

9. The method of claim 7 wherein determination of the capacitance at discrete locations along the vertical axis of the sample is made simultaneously.

10. The method of claim 7 which further includes positioning a hollow tube vertically through the interior of the sampling chamber;

arranging a plurality of capacitance indicators at spaced discrete locations vertically within said tube:

introducing a conductive fluid incrementally into the interior of said tube whereby the physical feature of the sample being measured is the capacitance of the well stream sample at predetermined level locations of the sample within the chamber, and the measurements are used to calculate fluid phase fractions of gas, oil and water in the well stream sample and the degree of oil-water emulsion in the sample.

11. The method of claim 7 which further includes positioning an electrically conductive hollow tube having an electrically nonconductive outer surface vertically within the interior of the sampling chamber;

positioning a plurality of capacitance indicators serially along the vertical length of said tube, and obtaining capacitance measurements from said indicators as the fluid sample fills the sampling chamber.

12. 20 method of claim 7 which further includes positioning an electrically conductive longitudinally extending probe vertically above the sampling chamber;

coupling a capacitance indicator to the probe, lowering the probe into the sampling chamber in a series of incremental steps, and obtaining capacitance measurements from said capacitance indicator as the probe is incrementally lowered into the fluid sample in the sampling chamber.

13. An arrangement for carrying out the method of claim 1 which comprises:

a phase separator means having an inlet and an outlet and which receives an oil well production fluid steam through the inlet and separates out a substantial portion of the gas fraction of the well stream and passes the resultant well stream out the outlet;

an outlet flow conduit connected to the outlet of the phase separator means;

a vertically disposed sampling chamber having predetermined height and other dimensions that is selectively coupled to the outlet conduit to permit a predetermined amount of resultant well stream to enter the sampling chamber and to trap a sample of the such well stream therein;

first measurement means coupled to the sampling chamber to determine a number of values relating to the sampled well stream;

second measurement means coupled to the sampling chamber to determine values relating to the permitivity of the sampled well stream at discrete locations spaced vertically through the height of the sampling chamber, and calculating means coupled to the first and second measurement means which uses the provided values to calculate the fluid phase fractions of gas, oil, and water and the oil-water emulsion in the well stream sample.

14. The arrangement of claim 13 wherein the second measurement means includes a hollow nonconducting tube which extends vertically through the sampling chamber;

a plurality of capacitance indicators that are positioned at spaced discrete locations in the interior of said tube, and means to reversibly incrementally introduce a conductive fluid upwardly into the tube whereby a plurality of capacitance values may be determined as the level of the conductive fluid incrementally raises within said tube.

15. The arrangement of claim 14 wherein the means to reversibly introduce a conductive fluid into the hollow tube includes a source of conductive fluid that is connected to the lower and upper ends of the hollow tube, and a reversible pump means that is interposed in the connection of the conductive fluid source to the lower end of the tube whereby the pump means may selectively raise or lower the height of the conductive fluid within the tube.

16. The arrangement of claim 15 which further comprises capacitance measuring circuitry that is coupled to the plurality of capacitance indicators;

a controller means coupled to the capacitance measuring circuity means for controlling the sequential determination of values from the first measurement means and the capacitance indicators, and the calculating means comprises a computer coupled to the controller and using the values provided thereby to compute the fluid phase fractions of gas, oil, and water and to quantify the degree of oil-gas emulsion in the well stream sample.

17. The arrangement of claim 13 wherein the second measurement means includes a hollow conductive tube having a nonconductive coating that is vertically positioned within the sampling chamber, and a plurality of capacitance indicators that are arranged at spaced discrete locations along the longitudinal height of the tube, whereby as the well stream sample is introduced into the sampling chamber and rises therein values of capacitance represented by the capacitance indicators may be determined.

18. The arrangement of claim 13 wherein the second measurement means includes a single elongate electrically conductive rod that is coated with a nonconductive dielectric coating and which is reciprocally positionable in the sampling chamber in the presence of a trapped well stream sample, and a capacitance sensing means that is electrically coupled to the rod so that as the rod is lowered into the trapped well sample values of capacitance are obtained as the rod passes through the gas, oil and water phases and emulsion interfaces of the well stream sample.

19. An arrangement for calculating the fluid phase fractions of gas, oil and water and the oil-water emulsion interface in an oil well stream which comprises:

an elongate vertically arranged sampling chamber having an inlet for receiving a well stream sample and an outlet for purging a sample from said sampling chamber;

an electrically nonconductive hollow tube extending vertically through the sampling chamber;

a source of pressurizable conductive fluid selectively connectable to the lower end of the hollow tube for selectively introducing such fluid into the tube while a well steam sample is present in the sampling chamber;

a plurality of capacitance indicators arranged at discrete spaced locations vertically within the hollow tube;

capacitance measuring circuitry electrically coupled to the plurality of capacitance indicators to generate values representative of changing capacitance as the fluid fills the chamber, and data processing means coupled to the capacitance measuring circuitry for utilizing capacitance values to compute the phase fractions of gas, oil and water and oil-water emulsion for a well steam sample.

20. The arrangement of claim 19 wherein the source of pressurizable conductive fluid includes a reservoir containing a conductive fluid that communicates with a reversible pump means for selectively filling the hollow tube with the conductive fluid when a well stream sample is present in the sampling chamber, and a controller means is coupled to the capacitance measuring circuitry and to the data processing means to control the recording of data and time information relating to the measurement of capacitance values for processing by the data processing means.

* * * * *